US012714398B2

(12) United States Patent
Ferrara et al.

(10) Patent No.: US 12,714,398 B2
(45) Date of Patent: Aug. 25, 2026

(54) PEDIATRIC VOLUMETRIC ULTRASOUND SCANNER

(71) Applicants: The Board of Trustees of the Leland Stanford Junior University, Stanford, CA (US); University of Southern California, Los Angeles, CA (US)

(72) Inventors: Katherine W Ferrara, Palo Alto, CA (US); Robert Gideon Wodnicki, Los Angeles, CA (US); Josquin L Foiret, Mountain View, CA (US); Eunyeong Park, Los Altos, CA (US); Anthony S Podkowa, Palo Alto, CA (US); Hanna Bendjador, San Francisco, CA (US); Wonseok Choi, Cupertino, CA (US)

(73) Assignees: The Board of Trustees of the Leland Stanford Junior University, Stanford, CA (US); University of Southern California, Los Angeles, CA (US)

( * ) Notice: Subject to any disclaimer, the term of this patent is extended or adjusted under 35 U.S.C. 154(b) by 0 days.

(21) Appl. No.: 18/559,135

(22) PCT Filed: May 16, 2022

(86) PCT No.: PCT/US2022/029421
§ 371 (c)(1),
(2) Date: Nov. 6, 2023

(87) PCT Pub. No.: WO2022/241308
PCT Pub. Date: Nov. 17, 2022

(65) Prior Publication Data

US 2024/0225601 A1 Jul. 11, 2024

Related U.S. Application Data

(60) Provisional application No. 63/188,881, filed on May 14, 2021.

(51) Int. Cl.
*A61B 8/00* (2006.01)
*A61B 8/08* (2006.01)
*A61B 8/14* (2006.01)

(52) U.S. Cl.
CPC .......... *A61B 8/4494* (2013.01); *A61B 8/0891* (2013.01); *A61B 8/145* (2013.01); *A61B 8/5223* (2013.01); *A61B 8/54* (2013.01)

(58) Field of Classification Search
CPC ..... A61B 8/4494; A61B 8/0891; A61B 8/145; A61B 8/5223; A61B 8/54; A61B 8/0825;
(Continued)

(56) References Cited

U.S. PATENT DOCUMENTS 4,185,501 A 1/1980 Proudian
4,641,660 A 2/1987 Bele
(Continued)

FOREIGN PATENT DOCUMENTS

JP 2004041730 A * 2/2004 ............. A61B 8/483

OTHER PUBLICATIONS

Tamamo et al., “3D Ultrasound Imaging System using Fresnel Ring Array & High Voltage Multiplexer IC”, 2004 IEEE Ultrasonics Symposium.

(Continued)

*Primary Examiner* — Kaitlyn E Sebastian
(74) *Attorney, Agent, or Firm* — LUMEN PATENT FIRM

(57) ABSTRACT

Ultrasound (US) imaging is scaled to arrays having a large number of elements. We use “active windows” to define the parts of the overall array that are active for transmission and reception. Each active window is 2D. Local electronics can move these active windows freely within the array, either together or independently. This effectively provides fast scanning by electronically moving the active windows around within a large stationary array. All of the elements
(Continued)

within an active window are individually controlled for beam forming, focusing etc. by beam forming electronics in the system controller. Thus there is no need to have all of the elements of the large, stationary 2D ultrasound array connected to the system controller.

15 Claims, 15 Drawing Sheets

(58) Field of Classification Search
CPC ..... A61B 8/085; A61B 8/0866; A61B 8/0883; G01S 7/52047; G01S 15/8925; G01S 15/8927; G01S 15/8993
See application file for complete search history.

(56) References Cited

U.S. PATENT DOCUMENTS 6,013,032 A * 1/2000 Savord ................ G01S 15/8927 600/443
7,021,143 B2 4/2006 Dasch
7,037,264 B2 5/2006 Poland
11,134,918 B2 10/2021 Wodnicki
11,199,625 B2 12/2021 Robert
11,534,131 B2 12/2022 Xie
2005/0288588 A1* 12/2005 Weber .................... A61B 8/483 600/447
2010/0168580 A1* 7/2010 Thiele ................. G01S 7/52095 600/447
2015/0245813 A1 9/2015 Towfiq
2015/0359512 A1* 12/2015 Boctor ................ G01S 15/8997 600/447
2018/0125446 A1* 5/2018 Boroczky ............ A61B 8/5223
2020/0046320 A1* 2/2020 Wodnicki .............. B06B 1/0622
2020/0205773 A1* 7/2020 Hynynen ............. A61B 8/4245
2021/0106305 A1* 4/2021 Wang ..................... A61B 8/466
2023/0182171 A1 6/2023 Henneken

OTHER PUBLICATIONS

Lee et al., “A Magnetic Resonance Compatible E4D Ultrasound Probe for Motion Management of Radiation Therapy”, 2017 IEEE International Ultrasonics Symposium (IUS).
Bailey et al., “A computer controlled transducer for real-time three-dimensional imaging”, 1991, Acoustical Imaging v18.
Kim et al., “Design and Test of A Fully Controllable 64x128 2-D CMUT Array Integrated with Reconfigurable Front-end ASICs for Volumetric Ultrasound Imaging”, 2012 IEEE International Ultrasonics Symposium Proceedings.
Kubota et al., “Imaging Flaws in Soldered Joints of Integrated Circuits Using an Ultrasound Electronic Scanning Technique”, 1992, IEEE Trans. UFFC, vol. 39, No. 1.
Thomenius et al., “Reconfigurable Mosaic Annular Arrays”, 2014, IEEE Transactions On Ultrasonics, Ferroelectrics, and Frequency Control, v61n7.

* cited by examiner

PEDIATRIC VOLUMETRIC ULTRASOUND SCANNER

CROSS-REFERENCE TO RELATED APPLICATIONS

This application is a 371 of PCT application PCT/US2022/029421 filed May 16, 2022. PCT application PCT/US2022/029421 claims the benefit of U.S. Provisional application 63/188,881 filed May 14, 2021.

STATEMENT OF GOVERNMENT SPONSORED SUPPORT

This invention was made with Government support under contract CA211602 awarded by the National Institutes of Health. The Government has certain rights in the invention.

FIELD OF THE INVENTION

This invention relates to volumetric ultrasound imaging. One example is large semi-cylindrical arrays for medical imaging, specifically where the fundamental imaging format is ultrasound combined with ancillary imaging methods.

BACKGROUND

Hundreds of millions of ultrasound (US) exams are performed each year worldwide. Advantages of US imaging include the low cost, lack of ionizing radiation, real-time visualization of anatomy and physiology, and the ability to guide interventions. In clinical practice the well-known applications of ultrasound have been for imaging the fetus in the womb, and in echocardiography. It is also well-known as a key technology for breast cancer diagnosis in callbacks due to its ability to differentiate fluid-filled cysts from cancerous tissue. Due to its low cost and portability, ultrasound has also recently been gaining interest as a general-purpose tool for general practitioners and emergency room settings. In addition, in recent years, significant interest in musculoskeletal use has been seen.

US is not currently used in clinical screening studies; enabling such studies would be transformative in clinical impact and reducing health care costs. In particular, due to its high resolution, real-time imaging capabilities and especially the lack of ionizing radiation, US has great promise as a general imaging modality both for abdominal diseases (e.g. kidney and liver cancers) as well as for imaging the limbs. The availability of a highly portable, real-time imaging tool, with high resolution, that rivals the volume image data sets which can be obtained using CT (computed tomography) and MR (magnetic resonance) but at a much lower cost and without radiation would offer a significant advance in imaging for general screening.

The current limitations for a general-purpose tool for general screening with US result from three key barriers: 1) the inability to rapidly acquire a 3D volume, 2) the tradeoffs between depth of penetration and resolution resulting from the diffraction limit, 3) the cost of implementing large two-dimensional (2D) arrays which could be used to generate volume datasets.

Therefore, there exists a need for a low cost and highly versatile imaging system for use in general diagnosis with 3D volume capability that is non-ionizing and that rivals or surpasses the resolution and accuracy of existing diagnostic and screening systems.

SUMMARY

To address the need for a low cost, non-ionizing volumetric imaging system, this work provides large semi-cylindrical arrays created using modular arrays of ultrasonic transducers and electronics to build successively larger and more complex imaging systems. This approach enables the acquisition of MR and CT format multi-slice volumes for general screening and diagnosis utilizing a low cost, highly portable, and real-time imaging modality, and eliminates concerns over ionizing radiation, and claustrophobia which are especially acute with the prior art systems (e.g. CT and MRI (magnetic resonance imaging), respectively).

In one embodiment, directly integrated switching electronics connected in arbitrary geometries, facilitates the development of inexpensive transducer array devices that scan 3D regions and can be adapted to many organ systems and clinical applications.

In another embodiment, the system insonifies planes, and spatial selectivity is achieved using receive beam-formation and compounding for high-speed abdominal imaging.

A preferred embodiment can include ubiquitous circuitry, applicable for a wide range of clinical applications (and therefore ultrasound center frequencies), mounted on modular transducer components. The array modules utilize composite material that improves bandwidth and sensitivity and can withstand higher temperatures associated with required parameters. The large array built up using these modules is interfaced to a massively parallel imaging system network (e.g. 2,048 channels or more) capable of realizing volumetric data acquisition in real-time.

In a further embodiment two-side tileable acoustic/electronic modules with interface electronics implemented using high density integrated circuits (ICs) and highly sensitive single crystal transducer material, are used to construct individual 2D array modules. These tileable array modules are tiled to form large array configurations such as a ring that can fit around a limb for musculoskeletal imaging.

In a further embodiment, the highly integrated ASIC (application specific integrated circuit) electronics accommodates linearly translating acquisition windows which acquire complete high-resolution slices with focusing in elevation, thereby providing excellent contrast to noise resolution (CNR) for optimized image quality. The translating acquisition windows operate similar to MR and CT in that they acquire complete slices through the imaged subjects which are then combined to yield highly detailed image volumes.

Individual transducer modules can be arrayed physically at angles to form curved transducer array structures in a piecewise linear fashion to further improve the focusing ability of the array and also to provide more conformal probe surface arrays for coupling to the body.

Individual system channels from a massively parallel (e.g. 2,048 or more processing channels) versatile programmable ultrasound scanner can be mapped to each array element in the electronically translating aperture.

Modular construction in the electronics and sensors can be used for improved yield and reduced cost. A large sensor array can be broken up into smaller (e.g. 16 by 16 element) modules composed of individual sub-arrays assembled to their associated interface electronics.

DETAILED DESCRIPTION

A) General Principles

Figure 1A:
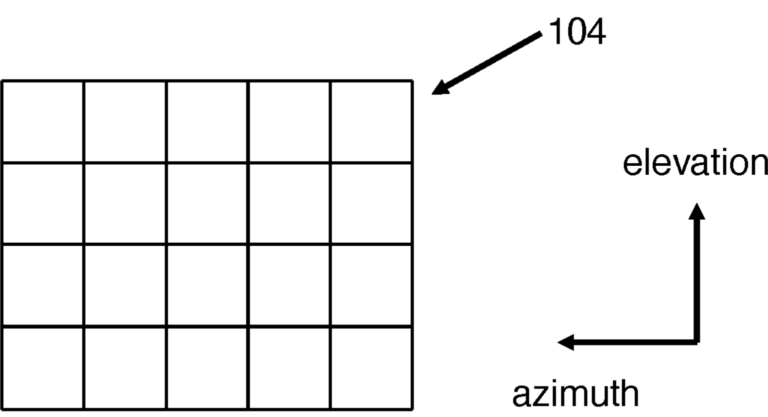
FIGS. 1A-B show one individual acoustic/electric module and the detailed construction therein.

It has long been known that imaging of a subject can, in principle, be done with a 2D ultrasound array where each element is individually controlled for beam forming etc. However, this approach is only practical for small arrays, where it is reasonable to make individual connections from each array element to a system controller for beamforming etc. This simple approach does not scale well to large arrays because of the large number of connections required. One practical approach that has been demonstrated for large arrays is known as local beamforming, where circuitry is disposed at or near the ultrasound array to locally perform beamforming operations, thereby reducing the number of required connections to the system controller. However, this approach requires significant compromises, since local beam forming circuitry is typically not capable of full independent control of all array elements.

In this work, a different approach is taken for scaling a 2D ultrasound array to a large number of elements. The key idea for controlling a large 2D array of ultrasound transducers in this work is to use "active windows" to define the parts of the overall array that are active for transmission and reception. Each active window is 2D. Local electronics can move these active windows freely within the array, either together or independently (i.e., reception can be at the same active window as transmission or at a different active window). This effectively provides fast scanning by electronically moving the active windows around within a large stationary array.

All of the elements within an active window are individually controlled for beam forming, focusing etc. by beam forming electronics in the system controller. The number of connections needed to the system controller is 1× or 2× the number of array elements in an active window, depending on whether reception is at the same window as transmission or at a different window. Thus, there is no need to have all of the elements of the large, stationary 2D ultrasound array connected to the system controller.

In a preferred operating mode of this system, the active windows are stripes whose long dimension is in the azimuthal direction and whose short dimension is in the elevation direction. The long dimension can be the full width of the underlying 2D ultrasound array. Electronic scanning of such active windows provides slice-by-slice acquisition comparable to image acquisition in MR or CT. Within such a slice, beam forming can perform functions such as focusing in elevation and/or azimuthal beam steering to provide high quality imaging. Azimuthal beamforming may be performed using planewaves.

B) Hardware Examples

B1) Problem Definition

Preferred embodiments relate to large semi-cylindrical arrays of ultrasound sensors with associated closely integrated sensing electronics that implement multiple imaging protocols for acquisition of 3D volumes in real-time for general-purpose diagnosis and staging of disease.

We can implement large area volume acquisition using plane wave transmission. While traditional US achieves spatial resolution by scanning the transmitted beam from one line of sight to the next (limiting abdominal imaging to an ~20 Hz frame rate and ~1 Hz volume rate); in this work, entire planes can be insonified, and spatial selectivity is achieved using receive beam-formation and compounding (a frame rate of 3800 Hz is feasible in abdominal imaging corresponding to a volume rate exceeding 20 Hz). To accommodate compounding, beam-steering up to 300 is included and a wideband material used. In the volume acquisition mode, this concept is further extended by transmitting multiple planes simultaneously. An Application Specific Integrated Circuit (ASIC) multiplexing and buffering matrix, interfaced with the transducer arrays facilitates beam formation approaches that realize large aperture arrays. In a preferred embodiment, e.g. manganese doped lead magnesium niobate-lead titanate (PIN-PMN-PT) modules of dimension 16 elements (azimuth) by 16 elements (elevation) are combined to form arrays of 128 by 256 (32, 768) or more elements. Here PIN is an acronym for lead indium niobate, PMN is an acronym for lead magnesium niobate, and PT is an acronym for lead titanate.

A goal of this work is to detect early disease in the general population, and therefore an intended application is to map anatomical and physiological changes with high spatial resolution. To that end, we describe 2D arrays with focusing in both elevation and azimuth and take advantage of wideband materials to reduce pulse length and thereby improve axial resolution. The effective electromechanical coupling coefficient (kt) for these composites ranges between 0.75 and 0.78 which is significantly higher than that seen using bulk lead zirconate titanate (PZT) (typically 0.4-0.6). We utilize such 1-3 composites of single crystal material with high effective kt to build transducers with wide bandwidth (to increase axial resolution) and improved penetration with greater sensitivity.

Modular construction in the electronics and sensors can be used for improved yield and reduced cost. We can break the array up into smaller (e.g. 16 by 16 element) modules composed of individual sub-arrays assembled to their associated interface electronics. Rather than requiring a single monolithic array of equally sensitive elements during manufacturing, modules can be selected for optimal performance during manufacturing and the array can be repaired by replacing modules. This feature reduces the cost of the complete large area probe since currently manufacturing transducers with uniform sensitivity is challenging and a modular damaged probe could be repaired and not replaced. With the present approach, the same ASIC modules can support multiple frequencies and array pitches of λ/4, λ/2 and λ. A single ASIC designed for imaging at multiple center frequencies (5.4 MHz, 2.5 MHz and 1.5 MHz) reduces the complexity and cost of the system implementation for multiple applications.

B2) Prior Work on Modular Arrays

In the prior art a limited number of high element count ultrasound arrays have been developed and described; however, they have incorporated micro-beamformers that prevent single channel data access and their proprietary ASICs in the transducer head prevent the incorporation of these arrays on open source programmable scanners. Micro-beamformers in the transducer head also reduce the number of cables and system channels (<192) to reduce cost and weight; however, this has limited new applications of ultrasound. Previous transducer designs, including sparse arrays, compromise on the number of active elements and image quality. Traditional US transducers have also been manufactured as one unit that is the complete width and height of the final imaging aperture, however this makes them more vulnerable to high yield loss which affects cost and image quality.

Modular, high channel count arrays have been investigated and have the potential to be transformative, when implemented in a clinical setting. The modular concept makes possible wide arrays for deep imaging and application tailored arrays that interface with programmable scanners. Such scanners offer 512-4,096 system channels, a broad range of imaging frequencies, arbitrary delays, apodization on all channels, large instantaneous dynamic range (14 bits) and programmable transmit waveforms.

Tiled modular 2D arrays with closely integrated ASIC electronics have been proposed for implementing large array apertures in multiple applications including obstetrics probes, cardiovascular imaging arrays, and diagnostic arrays for breast cancer. An important advantage of the modular approach is the ability to screen out low yielding 2D array modules with integrated electronics prior to assembly in order to realize high aggregate yield of the completed large aperture at reduced cost. An important consideration is alleviation of the routing bottleneck between the dense array of transducer elements and the lower channel count ultrasound imaging system. This has been resolved using locally integrated ASICs. 3D printed interposers integrated directly with the acoustic array provide an approach for high density assembly to ASICs, PCBs and flex circuits with reduced ringing and increase bandwidth.

B3) The Present Approach

To address the needs for a large array for general imaging in real-time, this work utilizes a modular approach and flexible electronic scanning to build flat or curved arrays capable of producing 2D slices through the anatomy which are then merged to create highly detailed imaged volumes. Using a staged process to minimize risk, individual tileable 2D array modules are built and validated. These validated modules are tiled up to form the large array interfaced to a networked array of massively parallel ultrasound system channels with a total channel count of e.g. 2,048 or more instantaneous imaging elements, and an overall array element count of e.g. 32,768 or more.

Figure 1B:
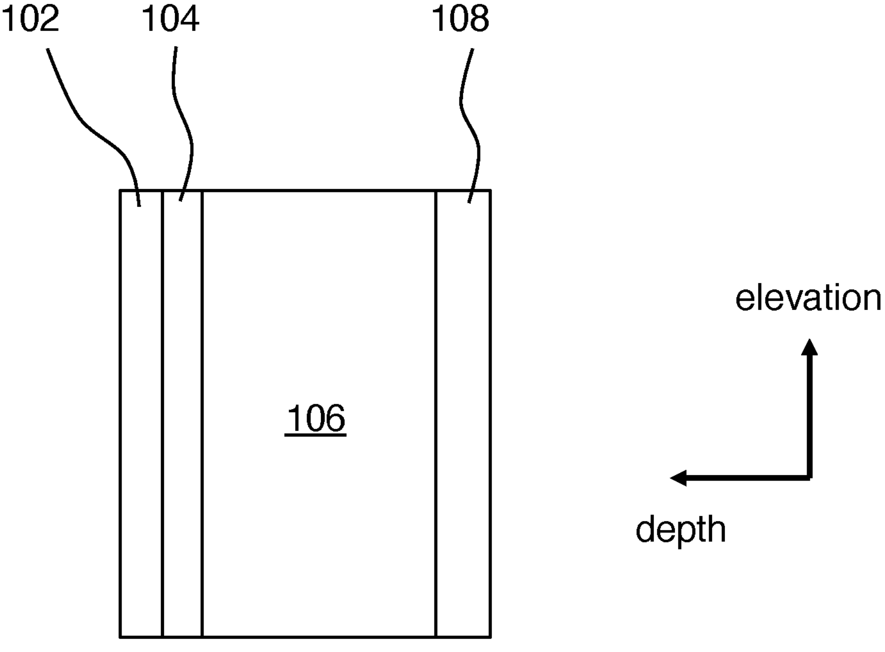

In FIGS. 1A-B, an exemplary individual acoustic module is shown, including a suitable acoustic backing 106, and an array of transducers 104 composed of sub-diced piezo and acoustic matching materials 102. In a preferred embodiment, the piezo material is a single-crystal composite of PIN-PMN-PT material with a suitable polymer matrix filling the interstitial kerfs. This piezo material has high electromechanical coupling coefficient, kt, which leads to high bandwidth and in turn realizes excellent axial resolution. The PIN-PMN-PT material also has a high Curie temperature which ensures that the material will not de-pole during regular use. For simplicity the front view of FIG. 1A shows transducers 104, even though they would be covered in this view by acoustic matching material 102.

In one embodiment, the acoustic backing 106 is comprised of a 3D printed interposer that maps the individual transducer elements to respective local electronics channels 108 at the back of the module. In an alternate embodiment, a solid backing is used with a flexible printed circuit (FPC) that brings the element channels from the array to the individual processing electronics. For optimal signal integrity, the array elements are closely coupled to their individual channel electronics which reduces the effects of parasitic coupling and thereby improves SNR (signal to noise ratio).

In a preferred embodiment, the closely coupled local electronics implements high voltage multiplexing and signal buffering functions locally to greatly reduce the number of signal cables that must be brought back to the massively parallel beamforming system. This local reduction in number of instantaneous signal channels also reduces the processing requirements on the ultrasound system itself which reduces cost and complexity of implementation. In another embodiment, the local electronics implements local Analog to Digital Conversion (ADC) and the signals from the module are transmitted in digital format to the massively parallel signal beamforming system.

Figures 2A, 2B:
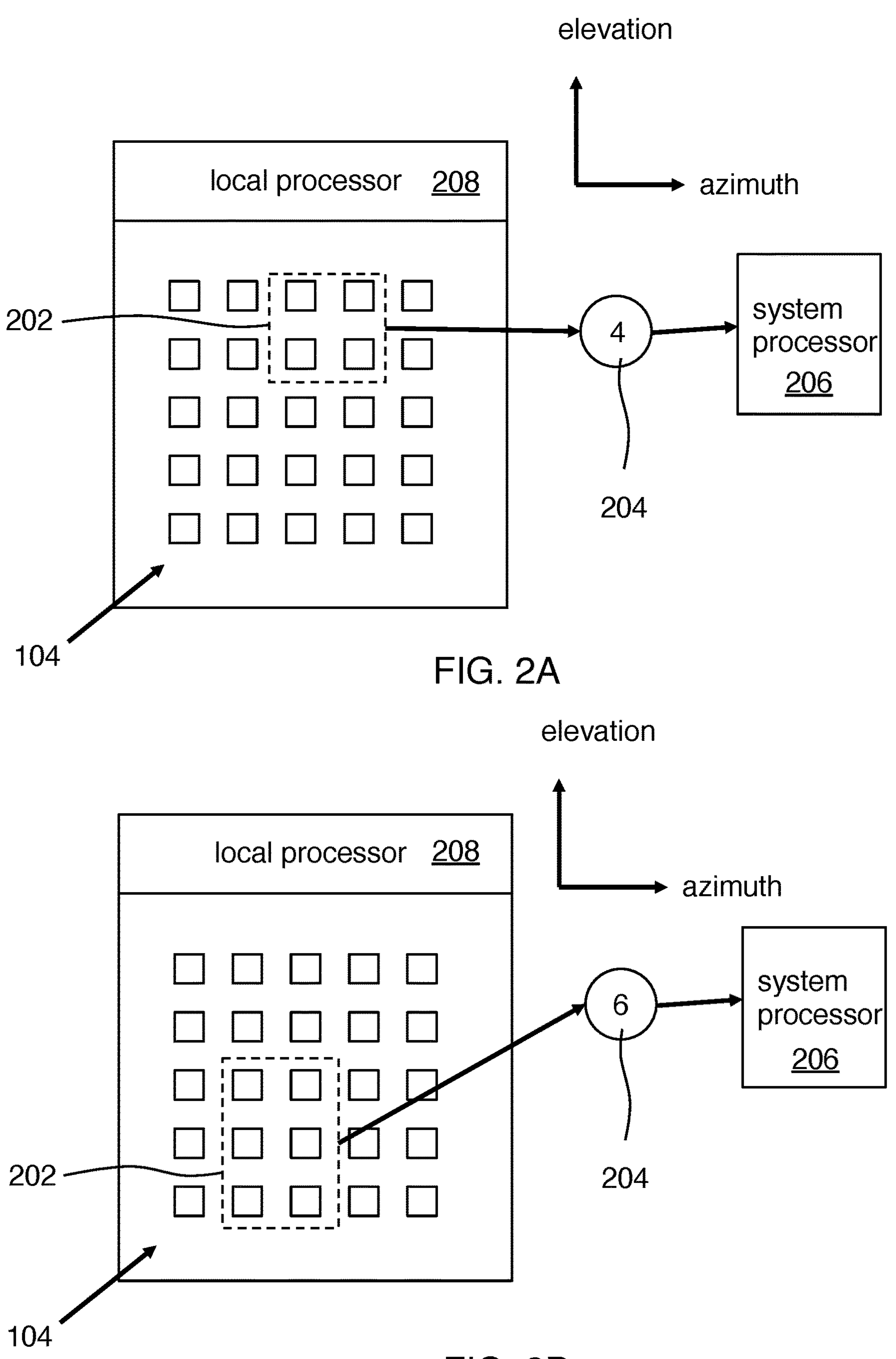
FIGS. 2A-B show an exemplary embodiment of the invention.

FIG. 2A shows an exemplary embodiment of the invention. This example is an apparatus including: a sensor array including at least one 2D array of acoustic transducer elements 104, a local processor 208 and a system processor 206.

The local processor 208 is disposed at the sensor array and is and configured to electronically define one or more active windows 202 within the sensor array. Here each of the one or more active windows 202 includes a corresponding 2D subarray of acoustic transducer elements of the sensor array (as shown). The one or more active windows 202 can be adjustably positioned within the sensor array by the local processor 208 (as shown in the difference between FIG. 2A and FIG. 2B), and only acoustic transducer elements that are within an active window are active for transmission and/or reception.

The system processor 206 has a fixed number of beamforming channels and is disposed away from the sensor array. The system processor 206 is configured to provide 2D beamforming by individual control of each acoustic transducer element that is within an active window. Finally, the system processor 206 is configured to tell the local processor 208 where to position each of the one or more active windows 202. Here 204 counts the number of connections between the sensor array and the system processor. This number is 4 and 6 in the examples of FIGS. 2A and 2B respectively. In general, the number of connections needed is the number of elements in all active windows in simultaneous use. One of the main points of this work is to provide practically useful and flexible beamforming without requiring all elements of the sensor array to be connected to the system processor.

Figure 6:
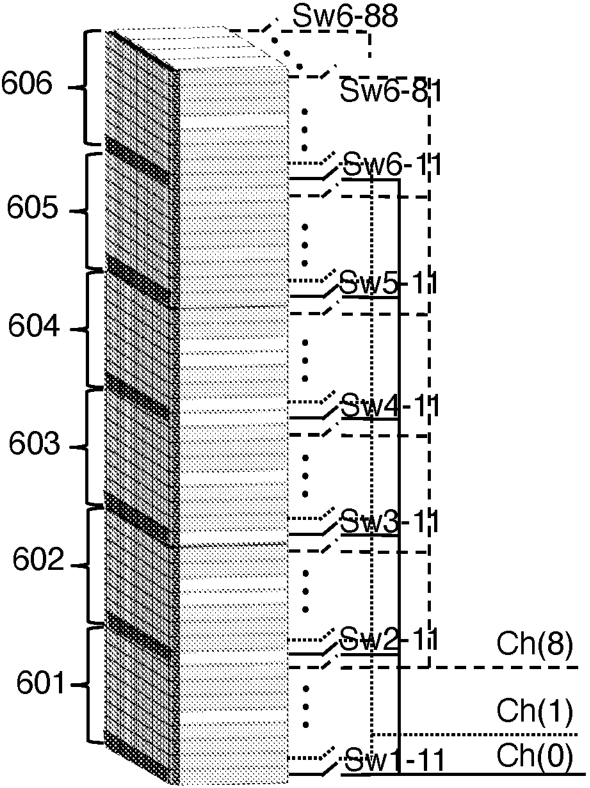
FIG. 6 shows an oblique view of a column of individual acoustic/electric modules and illustrates an exemplary network topology used to implement scanning of the contiguous acoustic aperture in the elevation direction

Each of the acoustic transducer elements within an active window can be uniquely connected to a corresponding one of the beamforming channels in the system processor by the local processor (see FIG. 6). The local processor can switch connections between the system controller and the sensor array to translate the one or more active windows in azimuthal and/or elevational directions (FIG. 6).

Figure 3:
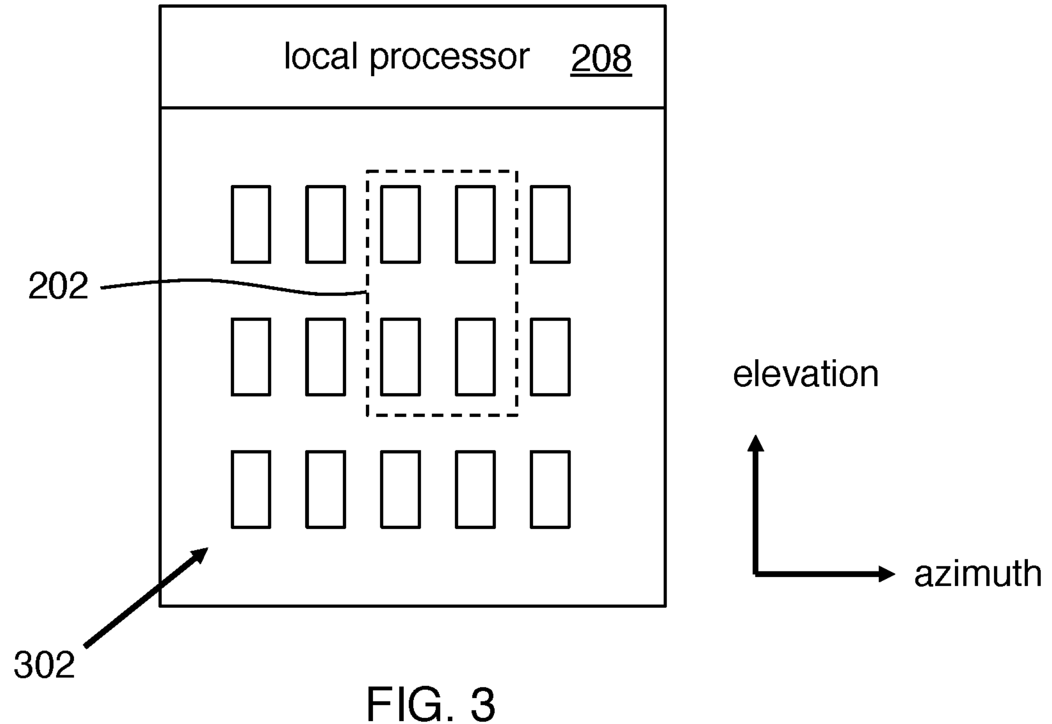
FIG. 3 shows a sensor array having a larger elevational pitch than azimuthal pitch.
Figure 4:
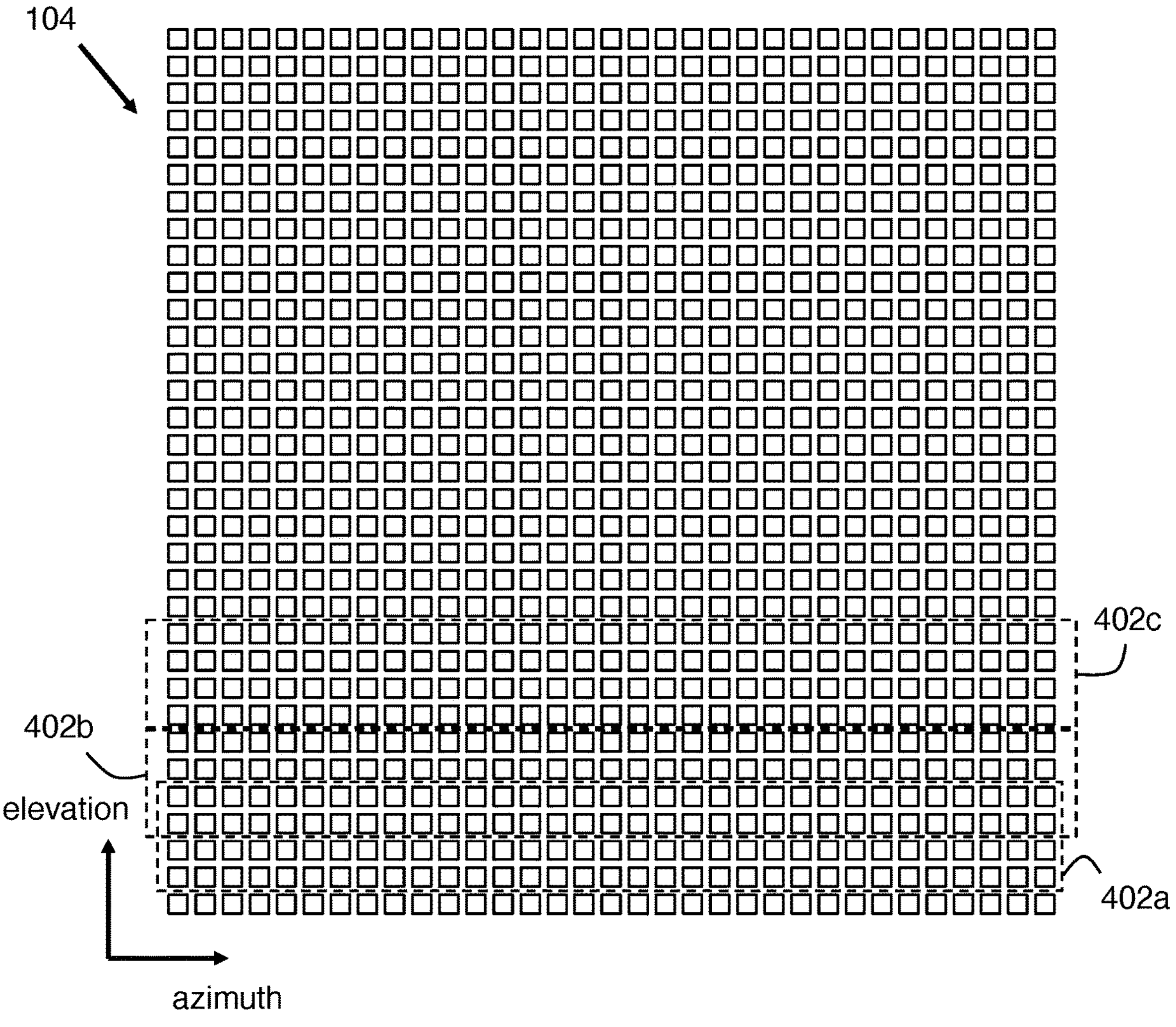
FIG. 4 illustrates scanning of the acoustic window by successive selection of contiguous groupings of ultrasound elements along the elevational length of the modular array.
Figure 12A:
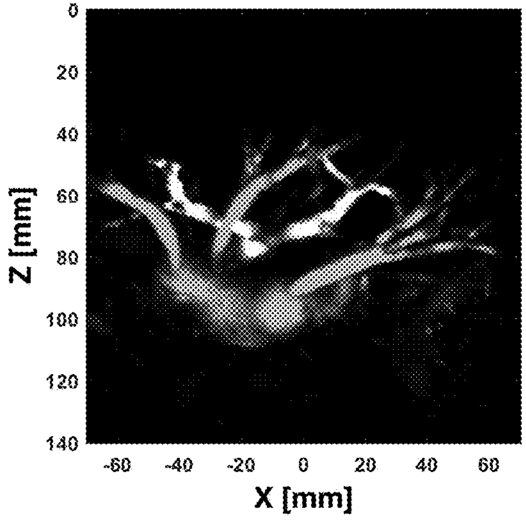
FIGS. 12A-B show two orthogonal views of a 3D blood vessel map obtained with an embodiment of the invention.
Figure 12B:
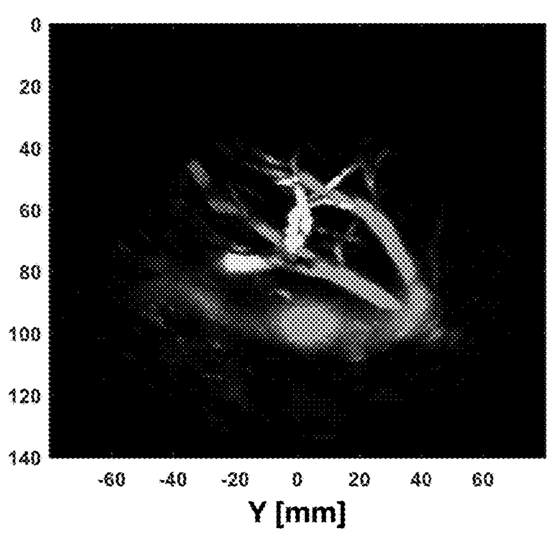
Figure 13A:
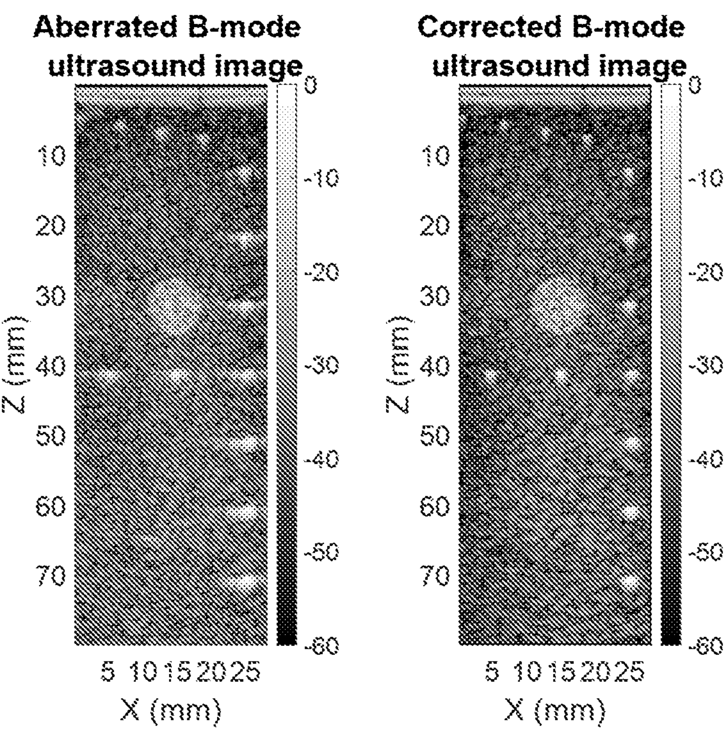
FIG. 13A shows the effect of a singular value decomposition correction on US phantom imaging in an embodiment of the invention.
Figure 13B:
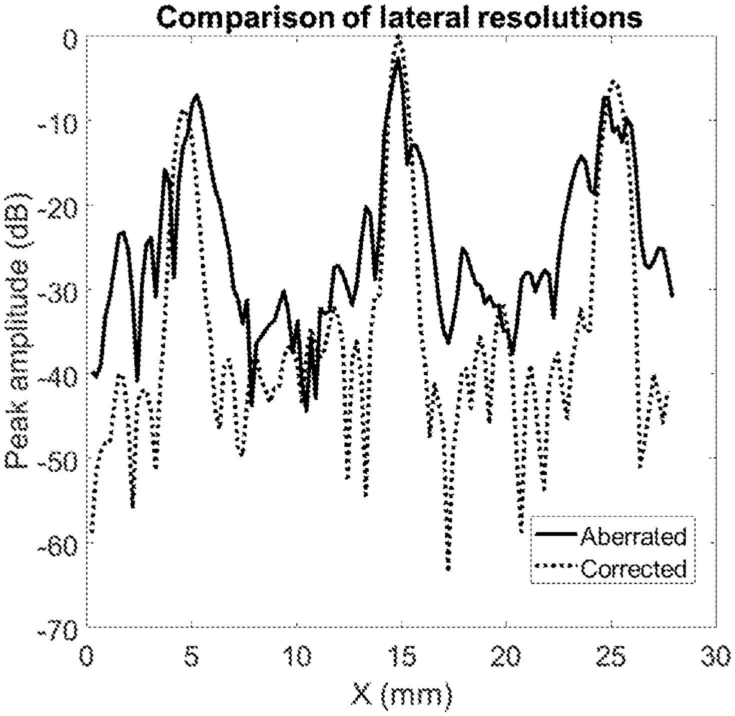
FIG. 13B shows the effect of the correction of FIG. 13A on lateral resolution.
Figure 14A:
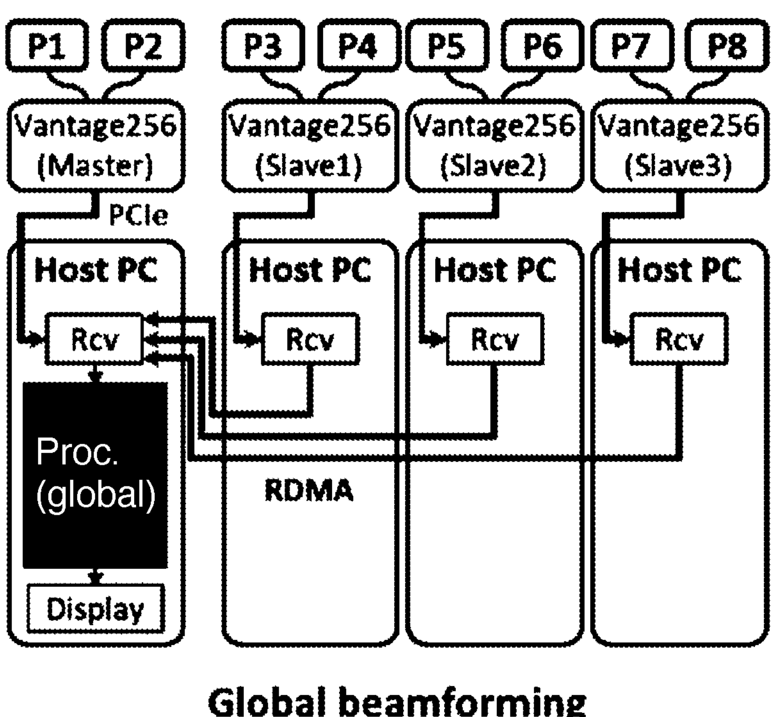
FIGS. 14A-B shows exemplary block diagrams for global and partial beamforming, respectively.
Figure 14B:
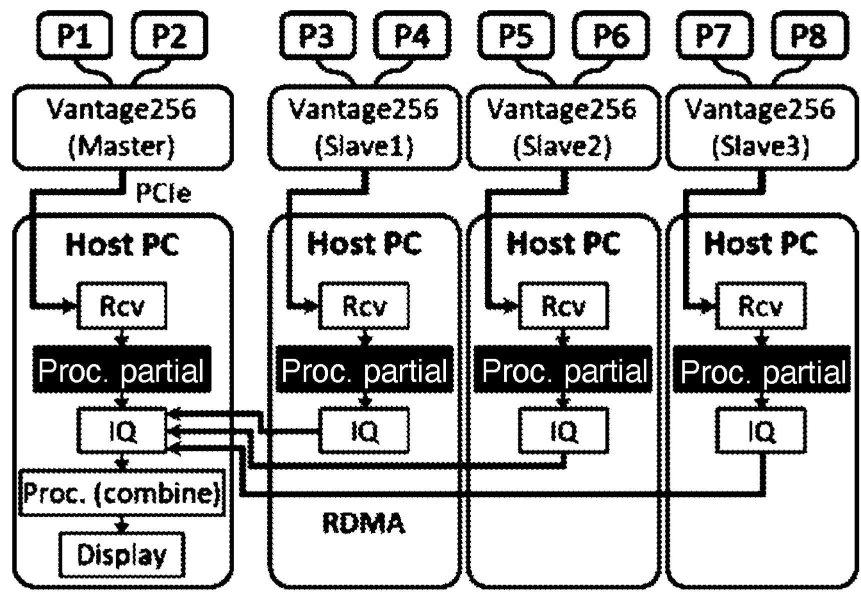
Figure 14C:
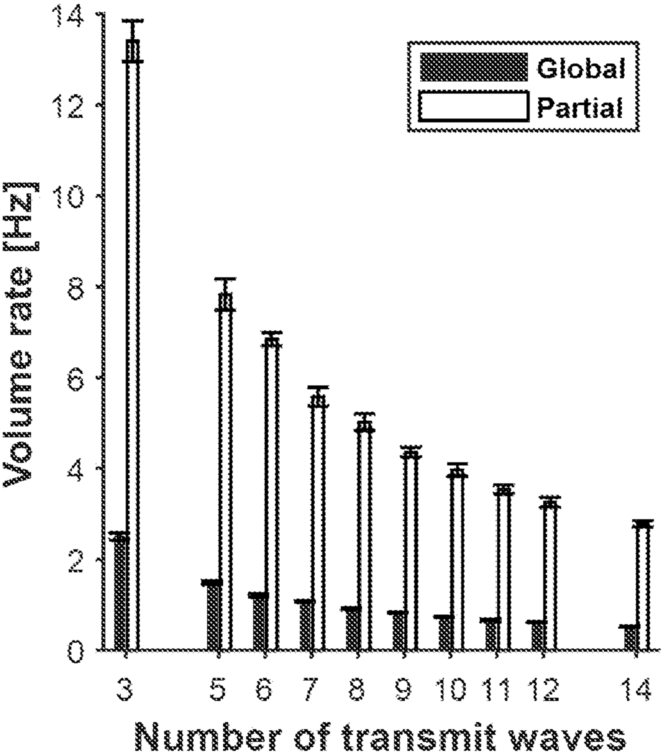
FIG. 14C shows acquisition rates for the two cases of FIGS. 14A-B.
Figure 15A:
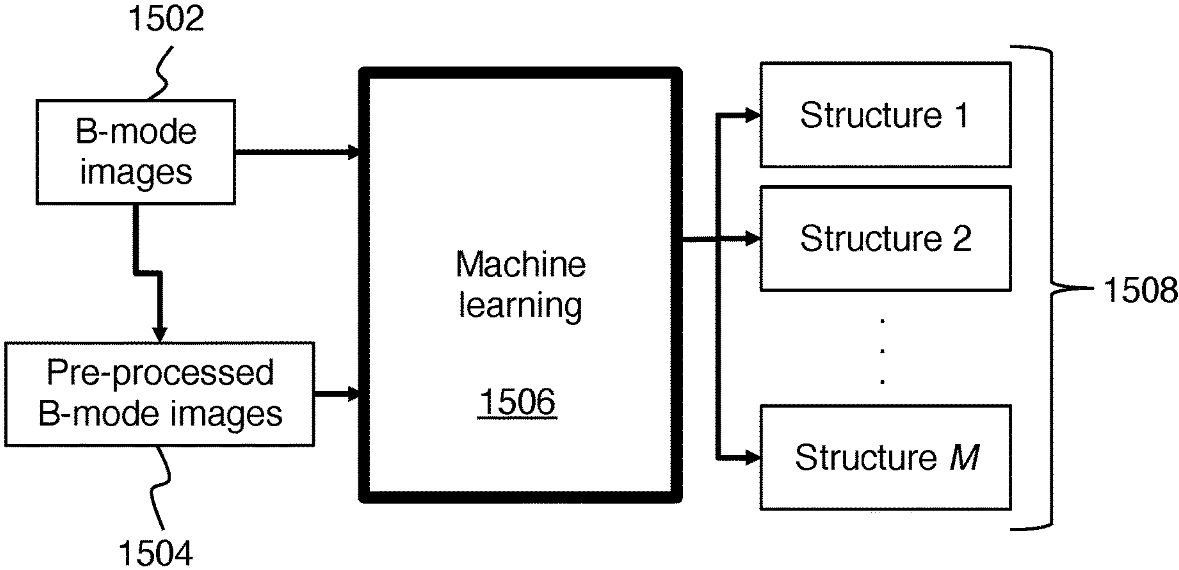
FIGS. 15A-B relate to machine learning in connection with embodiments of the invention.
Figure 15B:
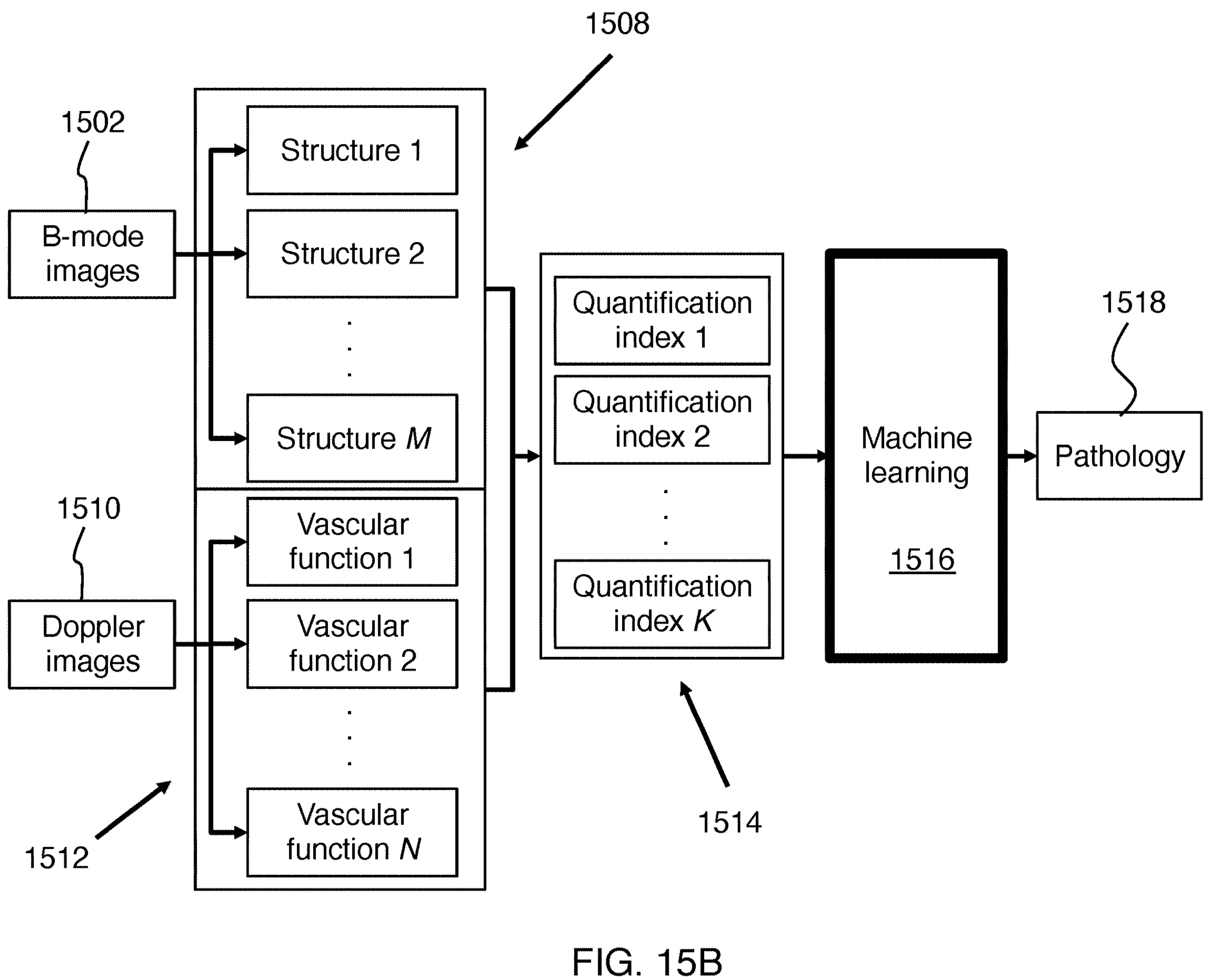

The sensor array can have a width W in an azimuthal direction and a height H in an elevation direction, the one or more active windows can be stripes having width W and having height h<0.25H (see the example of FIG. 4). The sensor array can have equal element pitch in the elevation direction and the azimuthal direction, as in the examples of FIGS. 2A-B. The sensor array can have a larger pitch in the elevation direction than the azimuthal direction, as in the example of sensor array 302 on FIG. 3. The system processor can be configured to perform tomographic reconstruction of an acoustic image from slice-by-slice data acquired by elevational scanning of the stripes along the height H. The tomographic reconstruction can provide visualization of blood vessels, in either Doppler or B mode imaging (FIG. 12). The tomographic reconstruction can include corrections for obstacles such as gas and bone utilizing advanced reconstruction techniques such as singular value decomposition (SVD) beamforming (FIGS. 13A-B). The 2D beamforming can include partial beamforming (FIGS. 14A-C). The system processer can include a machine learning system for recognition of organs and/or pathology (FIGS. 15A-B).

Figure 9:
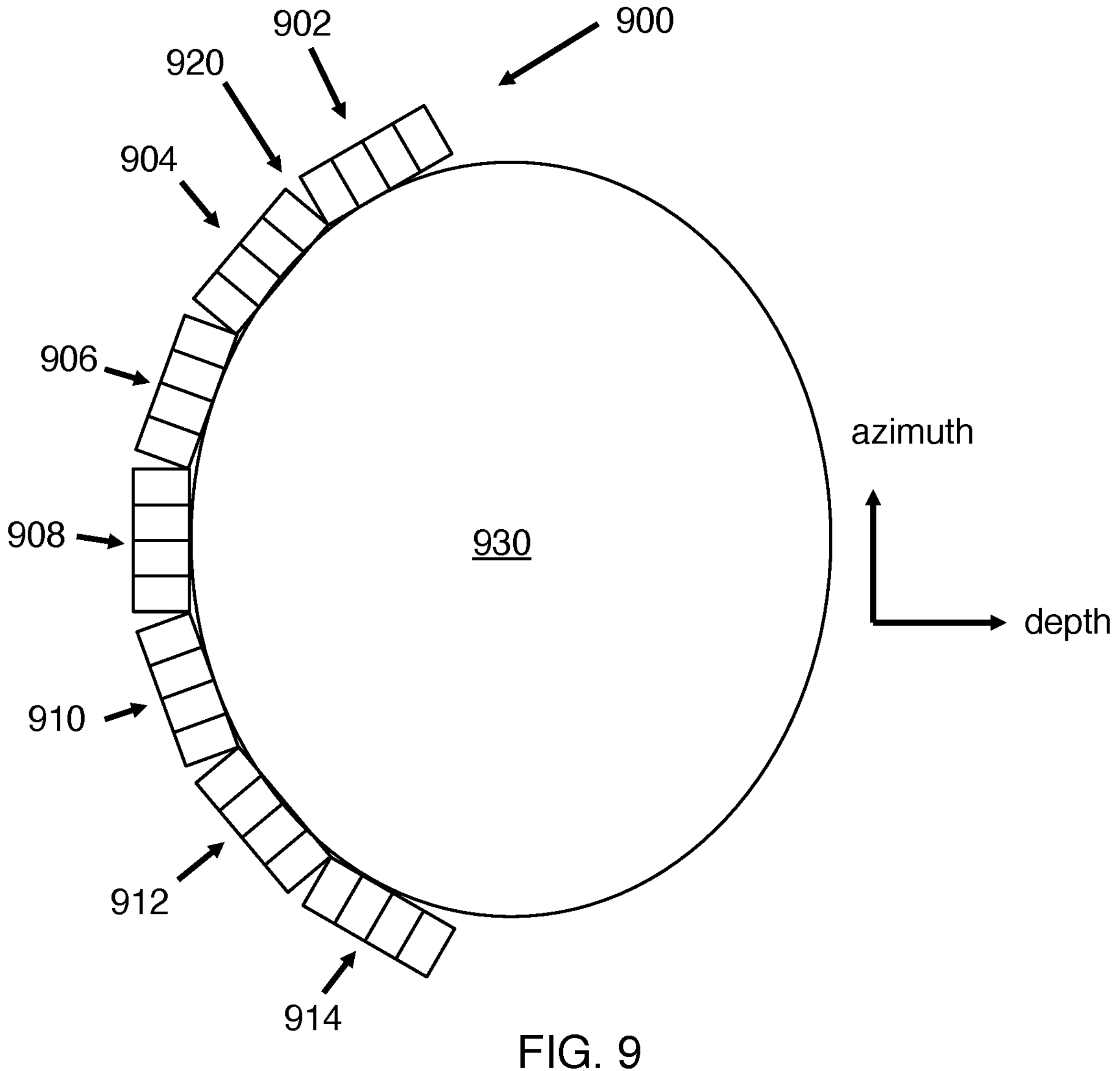
FIG. 9 illustrates the large area cylindrical array in a typical application for imaging the abdomen of a pediatric patient.

The sensor array can include three or more 2D arrays of acoustic transducer elements disposed in a curved array in an azimuthal dimension (FIG. 9).

Figure 10A:
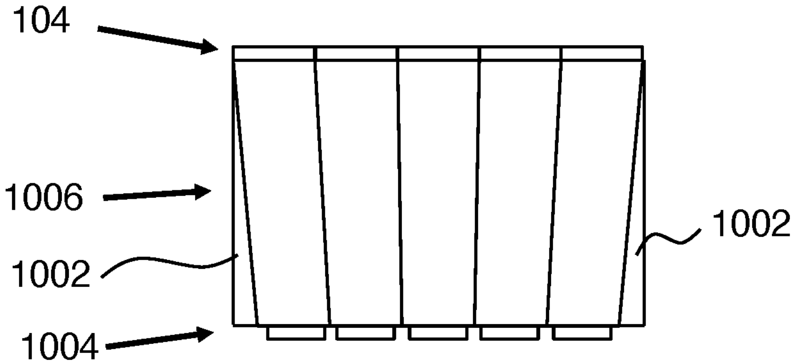
FIG. 10 illustrates the concept of interposer with sloping pillars to realize seamless tiling of the acoustic-electric modules in elevation and azimuth.
Figure 10B:
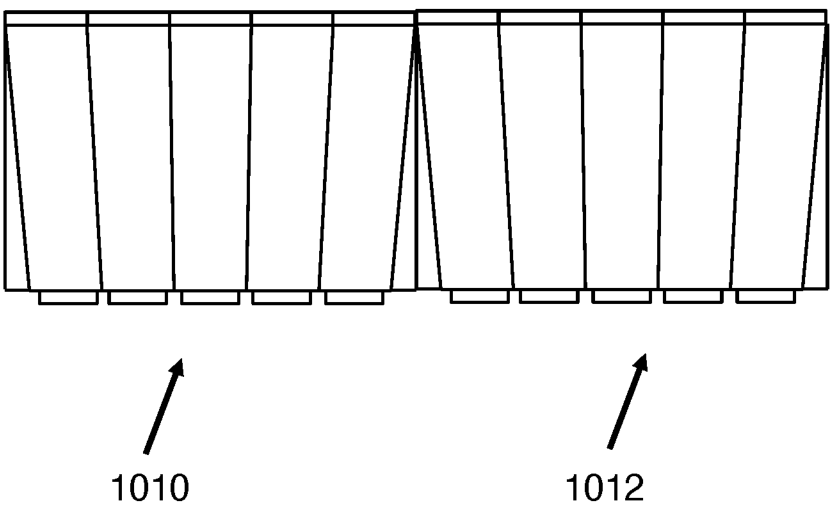

Each of the at least one 2D arrays of acoustic transducer elements can be included in a corresponding module, to make a modular sensor array (FIGS. 10A-B). The modules of a modular sensor array can include one or more sloping interposer pillars disposed between the acoustic transducer elements and backside connections of the modules. The result of this is the pitch of the backside connections being less than the pitch of the acoustic transducer elements, which facilitates close-packed tiling of the modules (FIG. 10B).

Figure 5A:
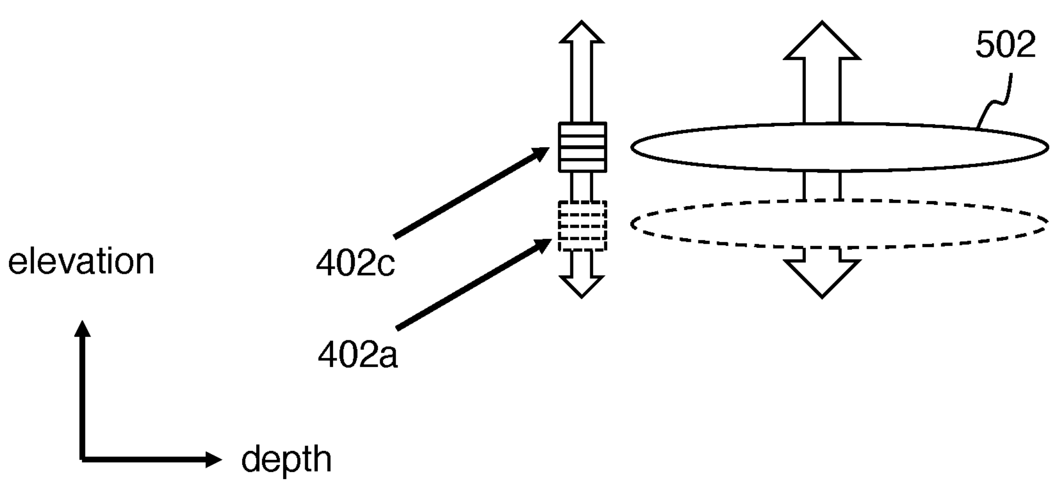
FIGS. 5A-B illustrate how the modular array creates a focused beam of ultrasonic energy that is oriented perpendicular to the array and finely focused in elevation.
Figure 5B:
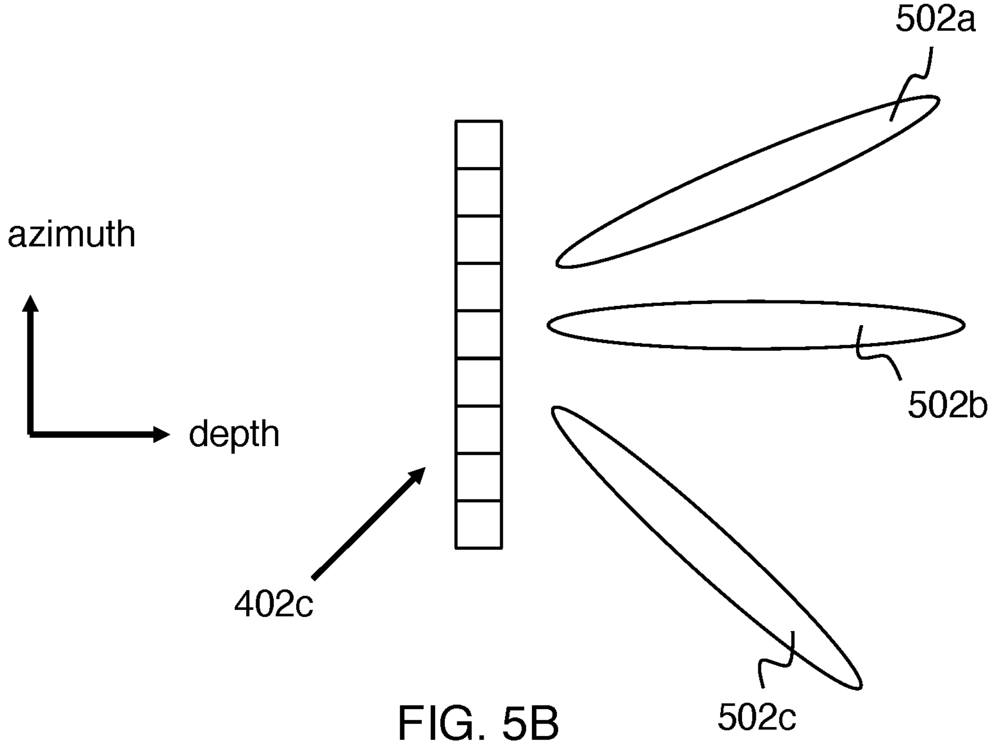

The system processor can be configured to implement plane-wave imaging by providing one or more linear phase gradients to acoustic transducer elements in active windows (e.g., the beam steering of FIG. 5B).

FIG. 4 shows another example of scanning an active window within a stationary sensor array. An instantaneous active window of elements 402*a* is active to create the beam at each scanning position. This active window can be scanned along the elevation dimension (e.g., to positions 402*b*, 402*c*, etc.), and the region of acquired slice data moves along with that window. Unlike CT or MR, these slices are scanned electronically and not by mechanically moving the patient.

The time to acquire a single slice is limited only by the time of flight of sound in the patient's body. For pediatric patients the imaged depth is shorter than in adults (roughly 50 mm, or 65 us total time of flight. By planewave imaging techniques, using 11 angles, each slice is acquired within e.g. 715 μs, for a total volume imaging time of 92 ms, or roughly 10 frames per second. In situations requiring faster frame rates (e.g. cardiology), we can reduce the number of angles to 5, and thereby obtain on the order of 20 fps. The large number of active channels in the azimuthal direction improves the ability of the array to focus at depth. The focused beam width is approximated as F #×λ, with in this case F # being ⅔, and λ equal to 300 μm. With this configuration, the described system achieves a focused beam width of 200 μm, with finer resolutions being obtained at more shallow depths as the F # is decreased. These numbers for real-time whole-body scanning are not possible with CT and MR, where single volume acquisitions are measured in minutes and resolution is measured in millimeters.

To achieve this very high speed of image volume acquisition, we utilize banks of massively parallel ultrasound system channels which are networked together and act essentially as an ultrasonic super-computer. The combined network may achieve real-time beamforming across e.g. 2,048 or more instantaneously processed transmit/receive channels. These 2,048 processing channels are electronically multiplexed to a contiguous active window of e.g. 256×8 transducer elements. Locally integrated ASICs which are part of the individual tileable imaging modules (discussed below) can implement the electronic scanning windows illustrated by 402*a*, 402*b*, 402*c* on FIG. 4 by reconfiguring the switch settings to route the 2,048 system channels to a different set of transducers at each slice acquisition.

As illustrated in FIGS. 5A-B, the large array operates by creating a translating focused beam 502 in elevation (FIG. 5A) which realizes an imaging slice through the patient anatomy, thereby providing excellent contrast to noise resolution (CNR) for optimized image quality. The translating focused beam operates similar to MR and CT in that it acquires complete slices through the imaged subjects which are then combined to yield highly detailed image volumes. For example, FIG. 5B schematically shows azimuthal beam steering to positions 502*a*, 502*b*, 502*c* that can be accomplished by beam forming with the system processor.

The detailed switching architecture for this scanning is illustrated in FIG. 6. For illustration, a bank of 6 modules (601, 602, 603, 604, 605, 606) is shown, where each module has an array of 8 by 8 transducer elements and corresponding switches. The switches are labeled according to the module and switch location within the module, Sw1-11 being the bottom right corner switch of module 601 and Sw6-88 being the top left corner switch of module 606 (switches Sw2-11, Sw3-11, Sw4-11, Sw5-11, Sw6-11, and Sw6-81 are also shown). Electronic scanning is accomplished as follows: The first slice is acquired with all 64 elements of module 1 being connected to Ch(0)-Ch(63). The next slice in the vertical direction is acquired by disconnecting the bottom row of elements of module 1 and instead connecting in the bottom row of elements of module 2 while still maintaining all the other rows of elements in module 1 connected to system channels. This is done by turning off Sw1-11 through Sw1-18 and then turning on Sw2-11 through Sw2-18. This process repeats successively with image slices being acquired at each vertical step, and the entire volume being reconstructed after all the slices have been acquired.

In a preferred embodiment, all of the switches illustrated in FIG. 6 are directly integrated locally with the transducer array either through connection using an interposer backing or through a flexible printed circuit (FPC). In this way the routing bottleneck from the transducers back to the system is greatly reduced. In this embodiment, the system includes high density, localized high voltage switching circuitry in ASIC form to multiplex thousands of 2D transducer elements to the e.g. 2,048 imaging channels of the programmable scanner network. The ASICs bring out a large number of channels simultaneously, thereby allowing for instantaneous sampling, without the requirement for local beamforming operation. The ASICs also implement buffer amplifiers behind each 2D element to match the high transducer source impedances to the cable and system front-end circuitry. The architecture implements multiple electronically swept protocols for fast 3D operation. Dynamic receive focusing in elevation significantly improves contrast resolution, particularly in the presence of aberrating fat and muscle layers. We can combine these ASICs with a PIN-PMN-PT array fabrication process to create modular wide bandwidth acoustic/ASIC array tiles. The described ASICs may be implemented in high quality processes for high voltage and mixed-signal applications including SOI (silicon on insulator), HV CMOS (high voltage complementary metal-oxide-semiconductor), Bipolar CMOS Double-Diffused Metal Oxide Semiconductor (BCDMOS), and GaN among others.

Figure 7:
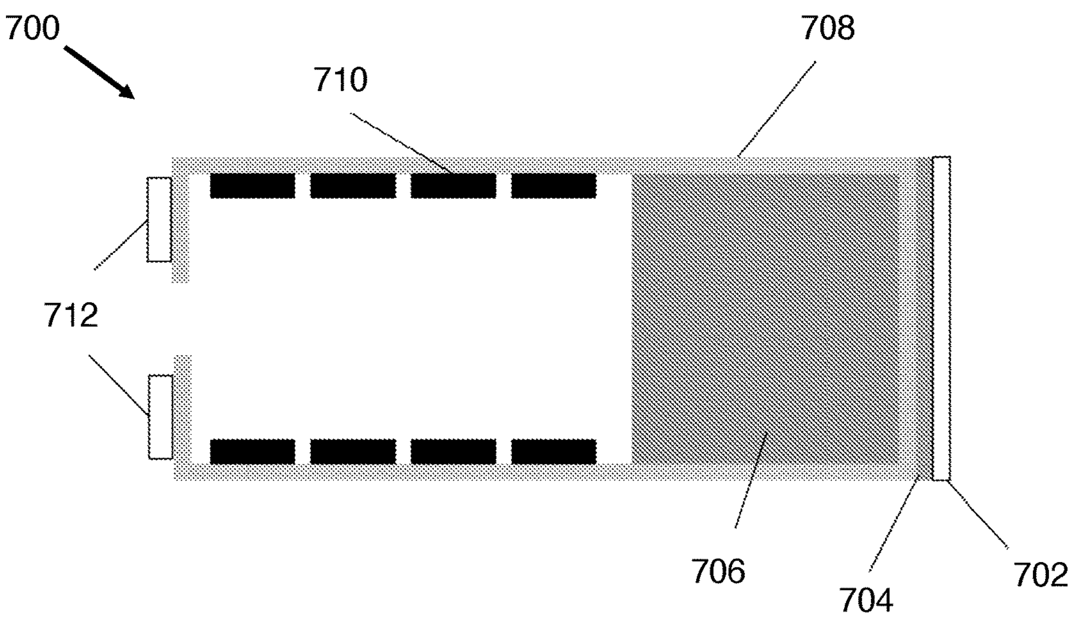
FIG. 7 shows a cross-section of a preferred implementation of the acoustic electric array module.

In a further embodiment, two-side tileable individual modules are used to create the large array. These modules are realized using 2D transducer arrays which are closely coupled to ASICs using high density flex circuits. FIG. 7 illustrates a cross-section of the construction of the two-side tileable modules 700. The acoustic stack for the modular high channel count array tiles operates at e.g. 4 MHz center frequency utilizing advanced 1-3 composites of PIN-PMN-PT material to improve the overall kt of the arrays for greater sensitivity and wider bandwidth. Quarter-wave matching layers 702 are used on the front of the array and a conductive composite material 706 is used as the backing layer. A rigid-flex circuit 708 brings the signal connections from the acoustic array 704 back to an array of multiplexing ASICs 710. The ASICs multiplex the system signal channels to the transducers and also provide buffering which performs electrical matching with the cable impedance for increased Signal to Noise Ratio (SNR) of the received signals. The output of this module is via mezzanine connectors 712.

Figure 8:
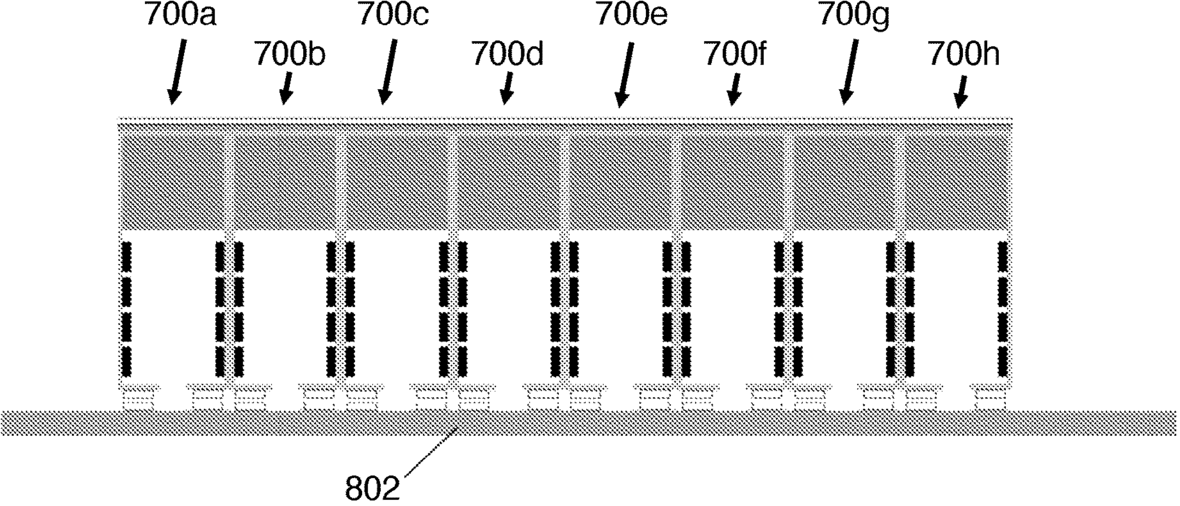
FIG. 8 illustrates assembly of multiple tileable acoustic/electric array modules supported by a bussing PCB (printed circuit board) substrate to create the large area array.

FIG. 8 illustrates the use of several acoustic modules as on FIG. 7 (700*a*, 700*b*, 700*c*, 700*d*, 700*e*, 700*f*, 700*g*, 700*h*) assembled onto a printed circuit board (PCB) 802. The flex circuits of each module are terminated in standard board to board mezzanine connectors (712 on FIG. 7) which then plug into a common backplane bus which in turn connects to the cable routing channels back to the system. A local FPGA (field-programmable gate array) controller (not shown) controls the ASICs and programs the correct bit patterns into the ASIC switches' on-chip RAM to setup the particular scanning configuration for each slice acquisition. In a preferred embodiment, the acoustic stack of FIG. 7 comprises an interposer backing 706 which brings the high density signals from the acoustic array to flex circuit connections for interfacing to the processing electronics.

In FIG. 9, one exemplary intended application is illustrated. In this case a pediatric patient 930 is imaged using a semi-cylindrical array 900 applied to the patient's abdomen. In this way fine detail of the abdominal organs can be imaged in 3D to aid in diagnosis. Here a grouping of modular sub-array building blocks (902, 904, 906, 908, 910, 912, 914) is tiled together to create an array with 512 elements in azimuth by 96 elements in elevation. The pitch in the azimuthal direction is 375 μm, corresponding to a 4 MHz center frequency for a linear array. The pitch in the elevation dimension is 938 μm, corresponding to an overall height for the array of 90 mm. The radius of curvature of the array 900 is an important parameter which affects the acoustic antenna gain at the focal point of the array and should also conform to the morphology of the patient's body.

In an embodiment, the radius of curvature is variable and can be adjusted to best fit the body habitus of the particular patient being imaged. As is illustrated in FIG. 9, the curvature of the aperture can be constructed through piecewise approximation by angular placement of the individual acoustic electric modules relative to one another. The angle of placement can be varied to adjust the radius of curvature. To accommodate different radii of curvature, the beamforming operation can also be adjusted with input from self-measurements of the array curvature or during manufacturing.

Physical gaps (e.g., 920) in the acoustic aperture due to tiling of the modules in the azimuthal and elevational dimensions can potentially contribute to imaging artifacts. In one embodiment, the beamforming process is augmented with a heuristic gap-filling algorithm which serves to ameliorate these effects. The combined imager operates as a 1.5D array with electronic focusing in elevation. The use of a 1.5D array is preferred for obtaining uniform slice thickness for excellent Contrast to Noise Ratio (CNR) and fine voxel definition throughout the depth of the acquired slices. In one embodiment, beamforming in the azimuthal direction is accomplished using multiple planewaves which are then summed to create high quality spatial compounded images. The architecture shown in FIG. 9 is similar to a CT or MR machine which acquires individual slices along the elevational length of the imaged subject.

An important consideration for a fully tiled array is to account for gaps between the individual modules, making these as small as possible. Frequently it is the backside connections and/or flex circuits 708 on FIG. 7 that would force modules to be spaced further apart than one would assume just from the acoustic transducer geometry. FIGS. 10A-B illustrate a preferred embodiment that minimizes gaps between modules to alleviate this issue. FIG. 10A shows a module having sloping interposer pillars 1006 connecting acoustic transducers 104 to backside connections 1004. These sloping pillars realize a pitch change from the top of the module to the bottom, as shown. This shrinks the footprint of the 2D array of connections which in turn allows the flex circuits (708 on FIG. 7) to occupy a smaller area. This embodiment also preferably includes a filler material 1002 to fill in gaps caused by the sloping pillars. FIG. 10B shows tiling of two adjacent modules 1010 and 1012 where each module is as shown on FIG. 10A.

In an embodiment, alignment procedures can be done to calibrate the locations of the individual modules in 3-space to ensure that the beam-forming coefficients line up correctly for constructive accumulation of the individual signals, for high quality and high-resolution beam-forming results.

In a preferred embodiment, B-mode imaging is used to realize image formation. In other embodiments a combination of coherent and non-coherent spatial compounding is used to optimize the balance between resolution and contrast in varying imaging conditions. Embodiments may also incorporate short-lag spatial coherence imaging to reduce clutter, and the large coherent aperture provides improved sensitivity to differences in coherence. In another embodiment, full synthetic aperture in elevation and/or azimuth is used to improve image quality by increasing the number of transmit/receive beamforming products in the overall beam summation process. In a further embodiment, Singular Value Decomposition (SVD) beamforming may also be used to improve the array's ability to reduce aberration due to fatty tissue layers in the body.

Embodiments can be designed to allow for the use of a range of operating frequencies such that it has wide applicability across tissue types and patient size. Rather than having multiple different ASIC designs with local micro-beamforming functionality where each addresses a specific frequency range (1.5 MHz for ARFI (acoustic radiation force impulse); 3 MHz-5 MHz for B-mode imaging), the modular architecture utilizes a single ASIC design across all frequencies. The ASIC can be designed at a specific pitch (e.g. 375 um for 4 MHz operation) and interfaced to a 1-3 composite that has a wide bandwidth covering the complete range of imaging frequencies. Lower frequencies are implemented by grouping adjacent elements electronically in the ASIC when selected by the user. In addition, the 2D array aperture of each module, with direct access to all elements, facilitates electronic focusing in elevation which reduces slice thickness and improves contrast resolution. Within a single scanning window, a programmable and flexible beamforming system (external to the array) has direct one-to-one access to all elements. In this way sophisticated and novel beamforming algorithms can be applied providing real-time and arbitrarily configurable beamforming coefficients on every element.

C) Results and Operation Modes

C1) Phantom Results

Figure 11A:
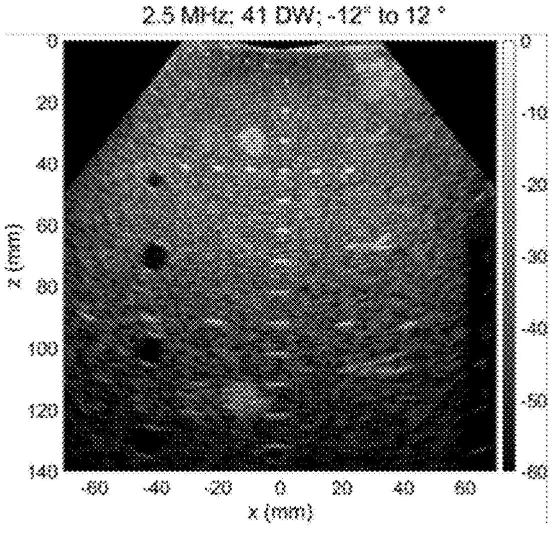
FIGS. 11A-B show a comparison of US phantom images from a commercial US system (FIG. 11A) and from an embodiment of the invention (FIG. 11B).
Figure 11B:
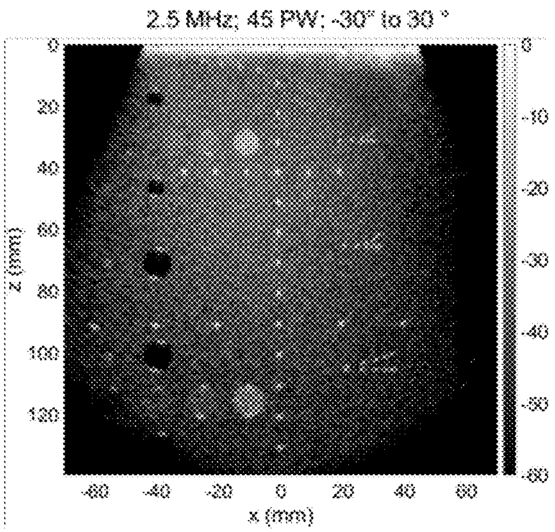

FIGS. 11A-B show a comparison of US phantom images from a commercial US system (FIG. 11A) and from an embodiment of the invention (FIG. 11B). Markedly better results are seen on FIG. 11B.

C2) Blood Vessel Mapping

One capability provided by this work is mapping blood vessels in 3D using either B mode or Doppler ultrasound images. FIGS. 12A-B show two orthogonal views of such a 3D map, where white is used to identify the portal vein and gray is used to identify the hepatic veins (right, middle, left).

C3) Gas and/or Bone Correction

Another capability provided by this work is correcting for obstacles such as bone and gas. The process of ultrasound image formation, so-called beamforming, can be expressed as an inverse problem in a mathematical formalism. Its ultimate goal is to retrieve, from the backscattered data, the actual structure of the medium that originated the waves. In all current clinical systems, the ultrasound image formation relies on the assumption of a homogenous medium. Though, the complexity and heterogeneity of human tissues and organs induce some deformation of the wavefront, called aberrations. Particularly, fat or bone layers strongly distort the image and hinders following quantitative assessments. The SVD (singular value decomposition) Beamformer is an ultrasound image formation technique that helps solve this issue by providing on one side the corrected image, and on the other side the amplitude and phase aberration correction. It is based on building a matrix of the different plane wave images, the Ultrafast Compound Matrix. Then, the mathematical operation of Singular Value Decomposition separates the angular and spatial variations such as:

$$IMAGE((x, y), \theta) = \sum_{i=1}^{N_\theta} \lambda_i U_i(x, y) V_i^*(\theta)$$

The first angular singular vector $V_1(\theta)$ gives the complex aberration law, and the first spatial singular vector $U_1(\theta)$ gives the corrected image. FIG. 13A shows the effect of this correction on aberrated phantom images. Importantly, the lateral resolution of point reflectors is greatly improved as seen in the plot comparison. This demonstrates the promising character of SVD Beamforming for in vivo high-resolution imaging, and for overcoming the long-time challenge of aberrations altering the image quality. FIG. 13B shows the effect of this correction on lateral resolution.

In order to maximize the statistical acoustic correlation from 2D plane waves propagating through the body, we adapt the SVD Beamformer approach for three-dimensional imaging. The formalism is transposed from a 2D cartesian space to 3D pixels in the Ultrafast Compound Matrix. This increases the data size, and both core CPU processing and parallel computing used to provide real-time processing of the volume formation. Singular Value Decomposition retrieves the corrected volume and adaptive processing applied to recover the anatomy.

The previous method also provides the expression of the deformation both in phase and amplitude ($V_1$). The amplitude data inform us on the ability of given plane waves to propagate through the medium. If gas or ribs are present in the medium and prevent one of them to propagate, the amplitude is reduced. Thus, we would be able to recover the signal in the shadowed region by considering only the non-zero amplitude plane waves and see through the obstacles. Further, the full 3D transducer and system may allow us to extrapolate holographic techniques to 3D.

C4) Partial Beamforming

Ultrasound (US) imaging has been routinely used for medical diagnosis and image-guided therapy thanks to the excellent safety, real-time imaging capability, and portability. New 1024 (or larger) channel imaging systems provide unprecedented opportunities to acquire data from 1D and 2D arrays with extended field-of-view (FOV) imaging. However, it is challenging to capture tissue motion or therapeutic procedures in real-time due to the enormous datasets. Here, we present a partial beamforming (BF) process with 1024-channel and multi-GPU cards for video-rate volumetric US imaging.

A 1024-channel research US platform (4 Vantage 256 systems, Verasonics Inc., USA) was used to drive a 2D matrix probe (64×16 matrix, Vermon, France; 64 (lateral)× 16 (elevation) elements, 0.65 mm×1.00 mm pitch). Each of the four systems P1, P2, P3, P4 has a GPU card (Titan RTX, Nvidia, USA) to accelerate processing. We report on a global BF process in which all RF data are transferred to and beamformed on the master system (FIG. 14A), and a partial BF process in which RF data are partially beamformed on each of the four systems and then transferred to and combined on the master system (FIG. 14B).

FIGS. 14A-B are block diagrams of B-mode ultrasound imaging on 1024-channel ultrasound platform with global beamformer (FIG. 14A) and partial beamformer (FIG. 14B). FIG. 14C shows average volume rate of global and partial beamformers for the 2D matrix probe with various number of transmit waves. The error bar represents standard deviation of 100 measurements. Here abbreviations and acronyms are as follows: PCIe, peripheral component interconnect express; RDMA, remote direct memory access; Rcv, receive buffer; Proc., process; IQ, IQ buffer.

The partial (global) BF achieved 13.4 (2.5), 7.8 (1.5), 5.6 (1.1), 4.4 (0.8), and 3.5 (0.7) volumes per second (vps) with 3, 5, 7, 9, and 11 plane waves with different steering angles from −10° to 10°, respectively (FIG. 14C). The size of RF data and FOV were 2304 (sample)×1024 (channel)×nTx (number of transmit waves)×2 byte and 6.1 cm (X)×2.2 cm (Y)×17.8 cm (Z), respectively. Using the partial BF process, we can achieve a much higher volume rate (>5.1× speedup) and generate identical beamformed results as the global BF process for the linear BF algorithm.

C5) Machine Learning

The system described herein can have more than 50000 elements, so clinical use can lead to a huge amount of data. In order to help doctors in extracting the most valuable information out of it, machine learning algorithms can be applied.

First, the machine learning framework can instantaneously assess the quality of the acquisition. We apply an algorithm for automatic detection of the system functionality including: skin-probe contact validation, data transfer validation, element transmission validation, missing frame detect. After performing a large number and variety of phantom acquisitions, we cluster the issues in system performance in different categories by segmenting the raw data. We use regression laws to link each anomaly to the corresponding issue by comparing linear classifiers (logistic regression or naïve Bayes) with K-means clustering techniques. These algorithms are then applied to identify the potential individual and cumulated acquisition defects in each set of acquisitions (unsupervised learning). Feedback will be provided in real-time to inform the clinician on the accuracy of the acquisition but will also be useful in post-processing, by for instance removing unexploitable regions.

Second, we can use the enormous amount of data generated by the system to create atlas libraries for pediatric ultrasound imaging of kidney, liver and hip. The intrinsic restriction of the patient population to small children will allow use of a database and will restrict the variability. We use a convolutional network to automatically extract the features in the ultrasound volumes and learn from them. Importantly, we will start training the network on our database to recognize anatomical boundaries of organs. Organ segmentation is the first step and will be enabled by the 3D torso cross sections obtained here. The CNN (convolutional neural network) will compare the voxel values to identify the objects and extract their shape. This will help doctors to orient the probe during acquisition and target the areas of interest.

In a later step, after a library of normal torso cross sections are obtained and the CNN trained, pathological features can be identified by convolving volumes with artificially generated kernels. These filters will be updated with each new set of data and the classification of anatomical structures will thus detect abnormal features.

FIGS. 15A-B show examples of the preceding ideas. FIG. 15A shows a learning set of B-mode images 1502 and pre-processed B-mode images 1504 that are both processed by the first machine learning block 1506 which produces Structures 1 . . . M (1508). Structures 1508 can be used to process new structural images of organs or can be later used to calculate a learning set for another machine learning block 1516 which produces Pathology 1518, as shown on FIG. 15B. Here the learning set of Quantification Indices 1 . . . K (1514) are calculated from the Structures 1 . . . M (1508) and Vascular Functions 1 . . . N (1512) from B mode images 1502 and Doppler images 1510, respectively. These Quantification Indices 1514 are processed by the second machine learning block 1516 to produce pathology 1518 of the imaged body.

The invention claimed is:

1. Apparatus comprising:

a sensor array including at least one 2D array of acoustic transducer elements;

a local processor disposed at the sensor array and configured to electronically define one or more active windows within the sensor array, wherein each of the one or more active windows includes a corresponding 2D subarray of acoustic transducer elements of the sensor array, wherein the one or more active windows can be adjustably positioned within the sensor array by the local processor, and wherein only acoustic transducer elements within an active window are active for transmission and/or reception;

a system processor having a fixed number of beamforming channels, and disposed away from the sensor array, wherein the system processor is configured to provide 2D beamforming by individual control of each acoustic transducer element that is within an active window, and wherein the system processor is configured to tell the local processor where to position each of the one or more active windows;

wherein the one or more active windows are freely defined by the local processor without reference to any division of the sensor array into fixed hardware-defined subarrays.

2. The apparatus of claim 1, wherein each of the acoustic transducer elements within an active window is uniquely connected to a corresponding one of the beamforming channels in the system processor by the local processor.

3. The apparatus of claim 1, wherein the sensor array has a width W in an azimuthal direction and a height H in an elevation direction, wherein the one or more active windows are stripes;

wherein a width of the stripes is W;

wherein a height h of the stripes is such that h<0.25H.

4. The apparatus of claim 3, wherein the sensor array has equal element pitch in the elevation direction and the azimuthal direction.

5. The apparatus of claim 3, wherein the sensor array has a larger pitch in the elevation direction than the azimuthal direction.

6. The apparatus of claim 3, wherein the system processor is configured to perform tomographic reconstruction of an acoustic image from slice-by-slice data acquired by elevational scanning of the stripes along the height H.

7. The apparatus of claim 6, wherein the tomographic reconstruction provides visualization of blood vessels, in either Doppler or B mode imaging.

8. The apparatus of claim 6, wherein the tomographic reconstruction includes corrections for obstacles selected from the group consisting of: gas and bone.

9. The apparatus of claim 1, wherein the 2D beamforming includes partial beamforming.

10. The apparatus of claim 1, wherein the system processer includes a machine learning system for recognition of organs and/or pathology.

11. The apparatus of claim 1, wherein the sensor array includes three or more 2D arrays of acoustic transducer elements disposed in a curved array in an azimuthal dimension.

12. The apparatus of claim 1, wherein each of the at least one 2D arrays of acoustic transducer elements is included in a corresponding module, whereby the sensor array is modular.

13. The apparatus of claim 12, wherein a selected module includes one or more sloping interposer pillars disposed between the acoustic transducer elements of the selected module and backside connections of the selected module, wherein a pitch of the backside connections of the selected module is less than a pitch of the acoustic transducer elements of the selected module.

14. The apparatus of claim 1, wherein the system processor is configured to implement plane-wave imaging by providing one or more linear phase gradients to acoustic transducer elements in active windows.

15. The apparatus of claim 1, wherein the local processor switches connections between the system processor and the sensor array to translate the one or more active windows in azimuthal and/or elevational directions.

* * * * *